(12) United States Patent
Lu et al.

(10) Patent No.: US 12,172,103 B2
(45) Date of Patent: Dec. 24, 2024

(54) ANTI-BIOFOULING MAGNETIC SILK FIBROIN (SF)-BASED COMPOSITE AEROGEL, AND PREPARATION METHOD AND USE THEREOF

(71) Applicant: Hefei University of Technology, Hefei (CN)

(72) Inventors: Yang Lu, Hefei (CN); Hanye Xing, Hefei (CN); Jingzhe Xue, Hefei (CN); Yonghong Song, Hefei (CN); Hao Xu, Hefei (CN); Sheng Chen, Hefei (CN); Kangkang Li, Hefei (CN); Liang Dong, Hefei (CN); Wei Zhang, Hefei (CN); Zongshun Peng, Hefei (CN); Lijing Wang, Hefei (CN)

(73) Assignee: Hefei University of Technology, Hefei (CN)

( * ) Notice: Subject to any disclaimer, the term of this patent is extended or adjusted under 35 U.S.C. 154(b) by 0 days.

(21) Appl. No.: 18/544,281

(22) Filed: Dec. 18, 2023

(65) Prior Publication Data

US 2024/0207756 A1 Jun. 27, 2024

(30) Foreign Application Priority Data

Dec. 21, 2022 (CN) .......................... 202211648303.5

(51) Int. Cl.
*C07K 14/435* (2006.01)
*B01D 1/00* (2006.01)
(Continued)

(52) U.S. Cl.
CPC ............. *B01D 1/30* (2013.01); *B01D 1/0035* (2013.01); *C02F 1/14* (2013.01);
(Continued)

(58) Field of Classification Search
CPC ........ C07K 14/43586; C07K 14/43518; C07K 17/04; H01F 1/344; H01F 1/36;
(Continued)

(56) References Cited

U.S. PATENT DOCUMENTS

2022/0185983 A1 6/2022 Kakali et al.
2022/0213173 A1 7/2022 Dietrich et al.
2023/0077045 A1 3/2023 Liu et al.

FOREIGN PATENT DOCUMENTS

CN 112915935 A * 6/2021 .......... B01J 13/0091

OTHER PUBLICATIONS

Machine translation of CN-112915935-A, 13 pages. (Year: 2021).*

* cited by examiner

*Primary Examiner* — Matthew E. Hoban
*Assistant Examiner* — Lynne Edmondson
(74) *Attorney, Agent, or Firm* — True Shepherd LLC; Andrew C. Cheng

(57) ABSTRACT

A magnetic material used in the magnetic SF-based composite aerogel is a ferroferric oxide nanocubic particle, which is a magnetic nanomaterial with both excellent magnetocaloric performance and excellent photothermal performance. The magnetic SF-based composite aerogel prepared by the present disclosure exhibits excellent responsiveness to both alternating current (AC) magnetic fields and sunlight. Under an action of an AC magnetic field, the magnetic SF-based composite aerogel exhibits excellent temperature rise performance, which can inhibit the generation of biofouling in pores and channels inside a three-dimensional (3D) porous evaporation material. The magnetic SF-based composite aerogel exhibits excellent water evaporation performance under a sunlight irradiation, with a water evaporation rate of 2.03 kg $m^{-2} \cdot h^{-1}$.

2 Claims, 19 Drawing Sheets

(51) Int. Cl.
    *B01D 1/30*            (2006.01)
    *C02F 1/14*            (2023.01)
    *H01F 1/34*            (2006.01)
    *H01F 1/36*            (2006.01)
    *C02F 101/30*        (2006.01)
    *C02F 103/08*        (2006.01)

(52) U.S. Cl.
    CPC .. C07K 14/43586 (2013.01); *C02F 2101/308* (2013.01); *C02F 2103/08* (2013.01); *C02F 2201/002* (2013.01); *C02F 2303/20* (2013.01)

(58) Field of Classification Search
    CPC ... H01F 1/37; H01F 1/38; H01F 1/047; H01F 1/0313; H01F 1/0054; H01F 1/0063; H01F 1/0081; C02F 1/14; C02F 1/48; C02F 2101/308; C02F 2103/08; C02F 2303/20

See application file for complete search history.

ANTI-BIOFOULING MAGNETIC SILK FIBROIN (SF)-BASED COMPOSITE AEROGEL, AND PREPARATION METHOD AND USE THEREOF

CROSS-REFERENCE TO RELATED APPLICATIONS

This application claims priority to Chinese Patent Application No. 202211648303.5 with a filing date of Dec. 21, 2022. The content of the aforementioned application, including any intervening amendments thereto, is incorporated herein by reference.

TECHNICAL FIELD

The present disclosure relates to the technical field of composite aerogel, and specifically to an anti-biofouling magnetic silk fibroin (SF)-based composite aerogel, and a preparation method and use thereof.

BACKGROUND

It has been proven that a macroscopic three-dimensional (3D) evaporator with a porous structure is a desired solar evaporator for water purification due to its advantages in light capture, heat insulation, and water transfer that can effectively improve an evaporation rate. During an actual water purification process, complicated contaminants in water have proven to be one of the most challenging issues for affecting the long-term durability of material and device.

Unlike inorganic salts, microorganisms are not only found in seawater, but also widely distributed in most natural water and wastewater. After attaching to a surface of an object, microorganisms will reproduce, differentiate, and secrete some polysaccharide matrices on the surface of the object to cause biofouling. For 3D porous evaporators, biofouling will cause blockage of pores to affect a moisture transfer and ultimately lead to a material failure. However, due to a limited penetration depth and energy density of sunlight, it is not enough to inhibit biofouling merely by relying on a photothermal effect (PTE) of an evaporator itself. Therefore, it is necessary to develop an anti-biofouling technology for 3D porous evaporators.

The magnetocaloric effect (MCE) is a heating means in response to an alternating current (AC) magnetic field by the magnetic material. Compared with PTE, MCE has advantages such as high heating rate, high thermal efficiency, and no restriction on a penetration depth. The MCE can achieve uniform heating overall. In addition, MCE is a remote and controllable heating method, which can allow heating as needed without moving an object and can control a heating temperature by changing the magnetic field intensity. Therefore, MCE makes it possible to control biofouling of pores and channels inside a 3D porous evaporation material. The use of MCE as a physical means to inhibit biofouling can reduce the dependence on chemical bactericides such as toxic cuprous oxide, and is a green and safe sterilization method.

In view of the above-mentioned basis, the present disclosure is finally provided through long-term research and practices of the inventors.

SUMMARY OF PRESENT INVENTION

An objective of the present disclosure is to solve the problem of reduction in the permeability of pores due to biofouling formed with the growth and reproduction of microorganisms inside a macroscopic 3D evaporator material with a porous structure., Embodiments of the present disclosure provide an anti-biofouling magnetic SF-based composite aerogel, and a preparation method and use thereof.

In order to allow the above objective, the present disclosure discloses an anti-biofouling magnetic SF-based composite aerogel, including an SF-aligned pore structure and magnetic nanoparticles (MNPs), where the MNPs are uniformly distributed in an inner pore of the SF-aligned pore structure.

The MNPs are ferroferric oxide nanocubic particles.

The anti-biofouling magnetic SF-based composite aerogel can allow a desired magnetocaloric biofouling-inhibiting effect when a concentration of the ferroferric oxide nanocubic particles is 1.0 mg/mL and a magnetic field intensity is 20 kA/m.

Under a light intensity of 1 kW/m$^2$, the anti-biofouling magnetic SF-based composite aerogel exhibits the optimal performance when a concentration of the ferroferric oxide nanocubic particles is 1.0 mg/mL, with an evaporation rate of 2.03 kg·m$^{-2}$·h$^{-1}$.

The present disclosure also discloses a method for preparing the anti-biofouling magnetic SF-based composite aerogel described above, including the following steps:

S1: preparing hydrophobic magnetic ferroferric oxide nanocubic particles by a high-temperature oil-phase method, and encapsulating the hydrophobic magnetic ferroferric oxide nanocubic particles with a polymer to obtain hydrophilic magnetic ferroferric oxide nanocubic particles;

S2: thoroughly mixing the hydrophilic magnetic ferroferric oxide nanocubic particles obtained in the step S1 with an SF solution to obtain a mixed solution;

S3: pouring the mixed solution obtained in the step S2 into a mold, conducting orientation freezing for 25 min to 35 min, and conducting lyophilization to obtain a first magnetic SF-based composite aerogel;

S4: soaking the first magnetic SF-based composite aerogel obtained in the step S3 in a methanol solution to allow immobilization to obtain a second magnetic SF-based composite aerogel; and S5: freezing the second magnetic SF-based composite aerogel obtained in the step S4 with liquid nitrogen, and conducting lyophilization to obtain the anti-biofouling magnetic SF-based composite aerogel for water purification.

In the step S2, a concentration of the hydrophilic magnetic ferroferric oxide nanocubic particles in the mixed solution is not greater than 2.0 mg/mL.

In the step S2, a concentration of SF in the mixed solution can be changed according to requirements for mechanical performance of a material, and the mechanical performance of the anti-biofouling magnetic SF-based composite aerogel gradually increases with an increase of the concentration of SF in the mixed solution.

In the S3, the orientation freezing is conducted with liquid nitrogen; and a temperature for the orientation freezing can be changed according to a required pore size, and a pore size decreases with a decrease of the temperature for the orientation freezing.

The present disclosure also discloses a use of the anti-biofouling magnetic SF-based composite aerogel described above in preparation of a solar-driven water treatment material.

In the anti-biofouling magnetic SF-based composite aerogel prepared in the present disclosure, a magnetic material is the ferroferric oxide nanocubic particle. Ferroferric oxide has excellent MCE and PTE. Strong magnetism can be used to inhibit the production of biofouling through MCE. After the magnetic SF-based composite aerogel undergoes a magnetocaloric treatment, *Escherichia coli* (*E. coli*) and *Staphylococcus aureus* (*S. aureus*) in pores inside the aerogel can be effectively inactivated, thereby inhibiting the mass reproduction of the bacteria inside the aerogel to cause biofouling and blockage of pores. The magnetocaloric assistance can effectively prolong a service life of the magnetic SF-based composite aerogel. The magnetic SF-based composite aerogel has unidirectional pores that provide channels for a water transfer, and a water evaporation rate of the magnetic SF-based composite aerogel under a sunlight intensity is as high as 2.03 kg m$^{-2}$h$^{-1}$. The magnetic SF-based composite aerogel exhibits a stable evaporation rate and recyclability when used to treat erythrosin or methylene blue (MB)-containing wastewater and simulated seawater. The SF-aligned pore structure can effectively immobilize the magnetic ferroferric oxide nanoparticles, such that a leakage rate of iron ions in the aerogel is extremely low under long-term immersion and compression, indicating that the aerogel has high stability. The magnetic SF-based composite aerogel has a low price, and is prepared by lyophilization, which is simple and easy to implement and facilitates industrial production.

Compared with the prior art, the present disclosure has the following beneficial effects: MCE is a direct heating method in which a magnetic material is used to generate heat and the heat can act efficiently on an inside of a 3D aerogel to effectively inhibit biofouling inside pores and thus make water channels unobstructed. The use of MCE as a physical method to inhibit biofouling can reduce the dependence on chemical bactericides such as toxic cuprous oxide, and is a green and safe sterilization method. The ferroferric oxide nanocubic particles have excellent photothermal conversion performance, and thus the single material allows two functions, which simplifies a preparation process and facilitates large-scale application.

DETAILED DESCRIPTION OF THE EMBODIMENTS

Figure 1:
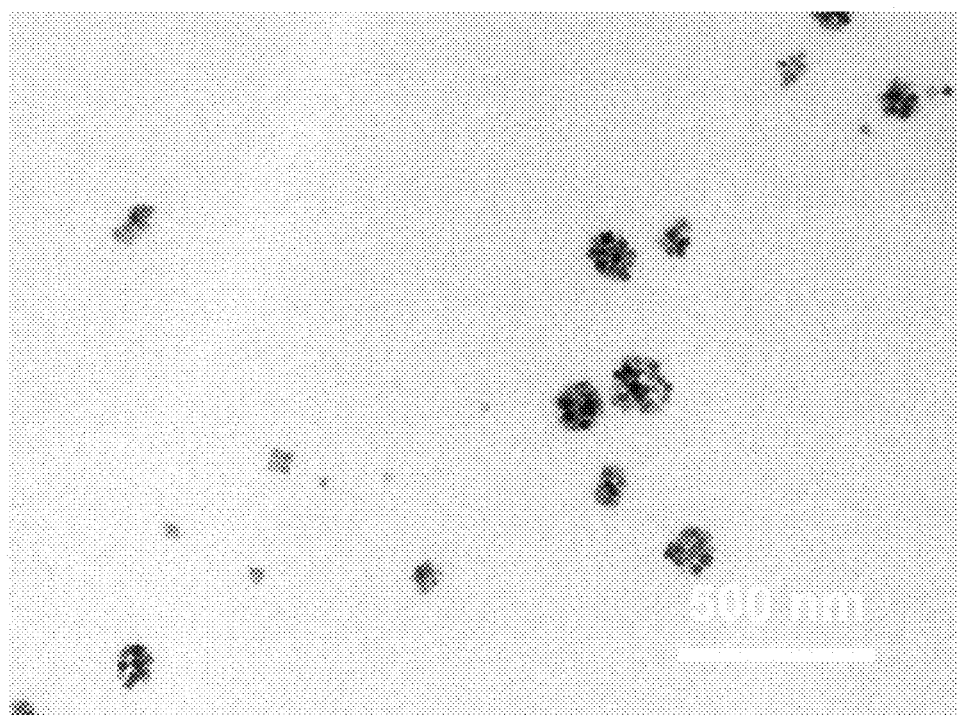
FIG. 1 shows a transmission electron microscopy (TEM) image of a magnetic SF-based composite aerogel.

The above and other technical features and advantages of the present disclosure will be described below in more details in connection with the accompanying drawings.

Example 1

Preparation of oil-phase ferroferric oxide nanoparticles: Iron acetylacetone (2.118 g) and biphenyl-4-carboxylic acid (1.2 g) were added to a mixed solution of oleic acid (3.81 g) and a benzyl ether (31.2 g). A resulting system was fully degassed, then heated to 290° C. and kept at this temperature for 30 min, cooled, and washed with methanol to obtain the oil-phase ferroferric oxide nanoparticles.

Example 2

Preparation of Aqueous-Phase Ferroferric Oxide Nanoparticles:

1) Polyacrylic acid (PAA) (0.1 g) was weighed and dissolved in 50 mL of a dimethyl sulfoxide (DMSO) solution to obtain a polymer solution.
2) 50 mg of ferroferric oxide nanoparticles were weighed and dispersed in 5 mL of chloroform to obtain a ferroferric oxide nanoparticle solution. Then the ferroferric oxide nanoparticle solution was added dropwise to the polymer solution obtained in the step 1). A resulting mixed solution was subjected to ultrasonic dispersion and then allowed to stand for 48 h.
3) A resulting system was centrifuged, and a resulting product was collected and stored in a vial.

Example 3

Preparation of Magnetic SF-Based Composite Aerogels:

1) The aqueous-phase ferroferric oxide nanoparticle sample prepared in Example 2 was tested for a concentration and then mixed with an SF solution having a mass fraction of 6%, and a resulting mixture was shaken up and down to allow thorough mixing to obtain a mixed solution. Through the above process, mixed solutions in which a mass fraction of SF was 4% and concentrations of ferroferric oxide nanocubic particles were 0 mg/mL, 0.2 mg/mL, 0.5 mg/mL, 1.0 mg/mL, and 2.0 mg/mL, respectively.
2) The mixed solutions were poured into a mold, subjected to orientation freezing on a cold plate for 25 min to 35 min, and then lyophilized to obtain preliminary magnetic SF-based composite aerogels.
3) The preliminary magnetic SF-based composite aerogels were soaked in a methanol solution to allow immobilization, and then the methanol solution in the preliminary magnetic SF-based composite aerogels was completely replaced with a tertiary butyl alcohol (TBA) solution.
4) The preliminary magnetic SF-based composite aerogels soaked in TBA were frozen with liquid nitrogen, and then lyophilized to obtain the magnetic SF-based composite aerogels.

FIG. 1 shows a TEM image of a magnetic SF-based composite aerogel, and it can be seen that clusters composed of ferroferric oxide nanoparticles are dispersed in the aerogel.

Figure 2:
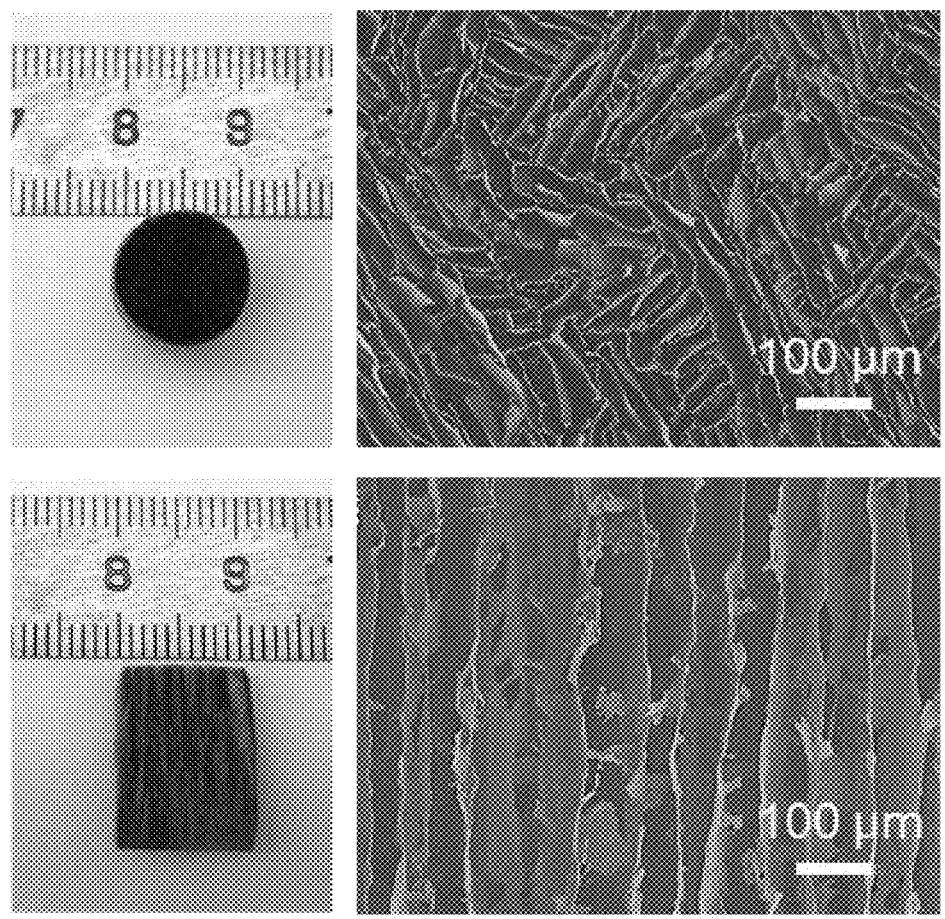
FIG. 2 shows scanning electron microscopy (SEM) images and optical images of a magnetic SF-based composite aerogel.

FIG. 2 shows optical images and SEM images of a magnetic SF-based composite aerogel, and it can be seen from the SEM images that pores in the magnetic SF-based composite aerogel have a length of about 100 μm and a width of about 20 μm.

Figure 3:
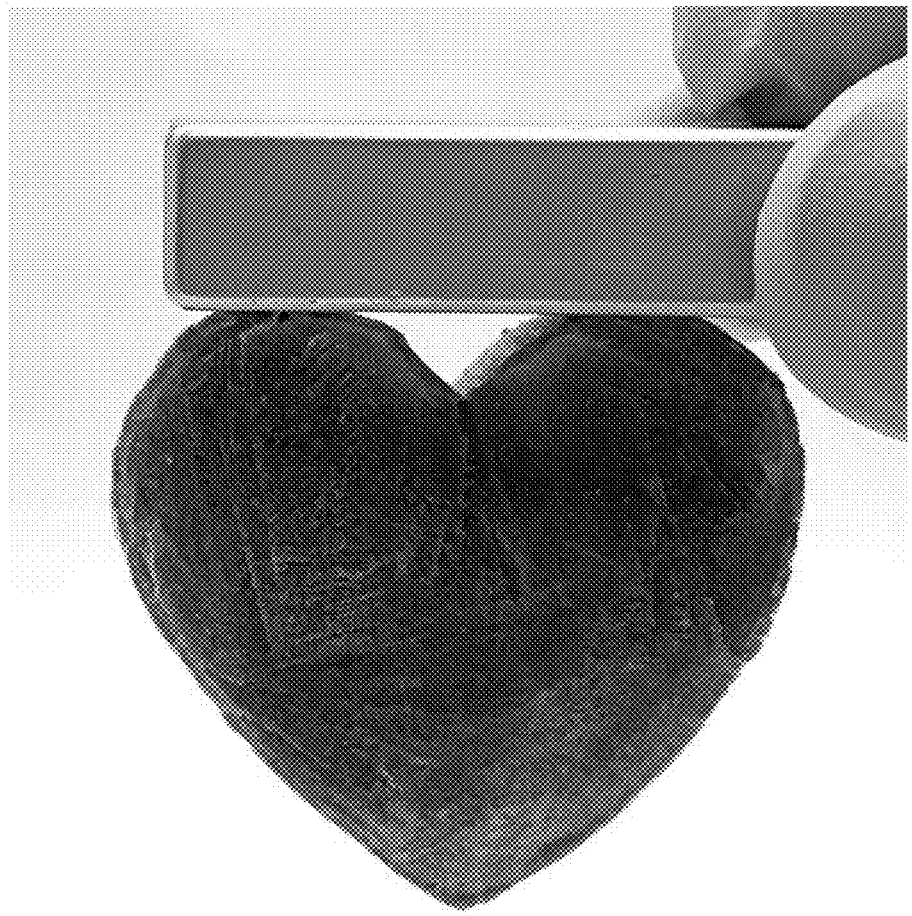
FIG. 3 is an image illustrating magnetic immobilization of a magnetic SF-based composite aerogel.

FIG. 3 is an image illustrating a magnetic field manipulation of a magnetic SF-based composite aerogel, and it can be seen that the magnetic SF-based composite aerogel can be immobilized and manipulated by a magnet.

Figure 4:
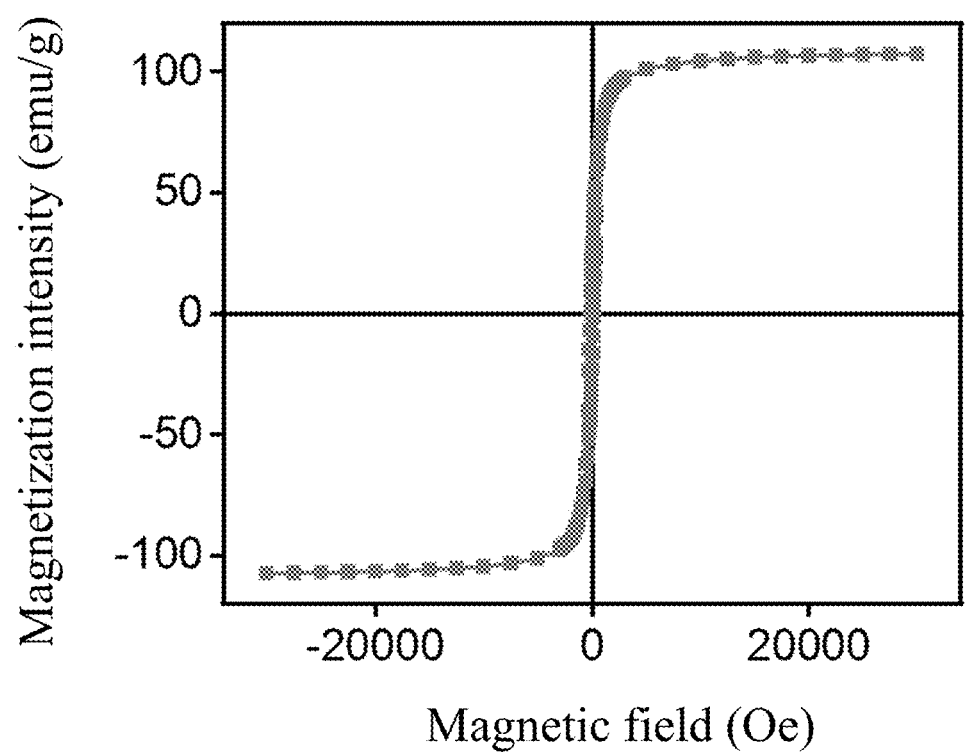
FIG. 4 shows a superconducting quantum interference device (SQUID) pattern of a magnetic SF-based composite aerogel.

FIG. 4 shows a SQUID pattern of a magnetic SF-based composite aerogel, and it can be seen from the SQUID pattern that a saturation magnetization intensity calculated based on an iron concentration is 107.4 emu/g.

Figure 5:
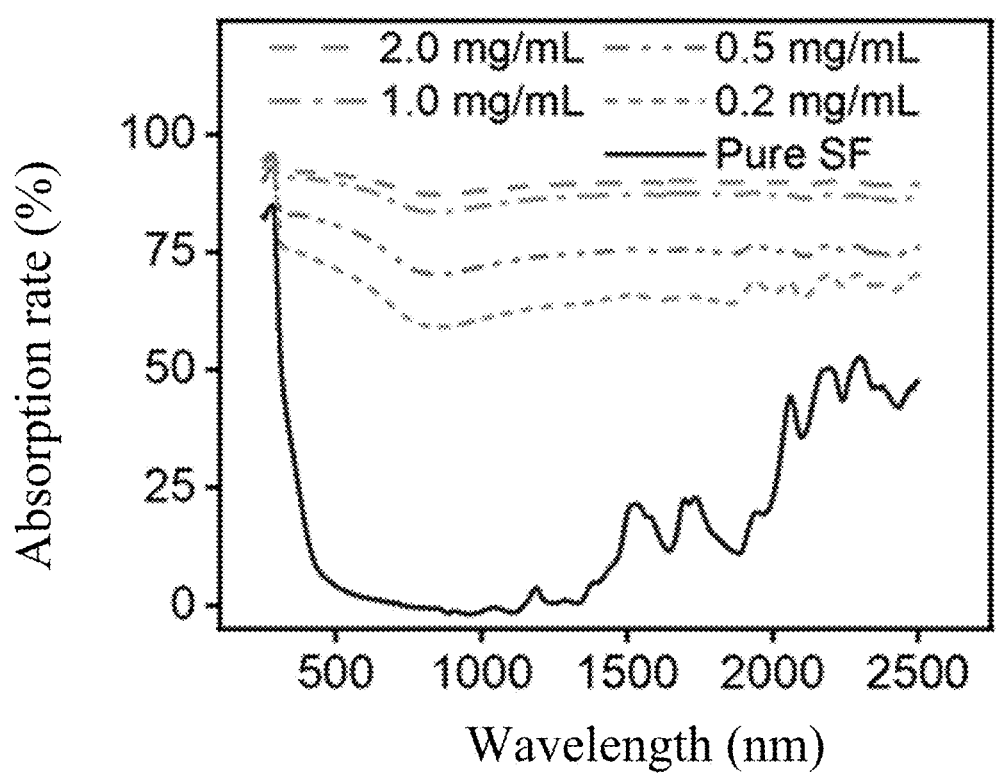
FIG. 5 shows optical absorption spectra of magnetic SF-based composite aerogels.

FIG. 5 shows optical absorption spectra of the magnetic SF-based composite aerogels, and it can be seen from the optical absorption spectra that the magnetic SF-based composite aerogels have excellent optical absorption performance.

Figure 6:
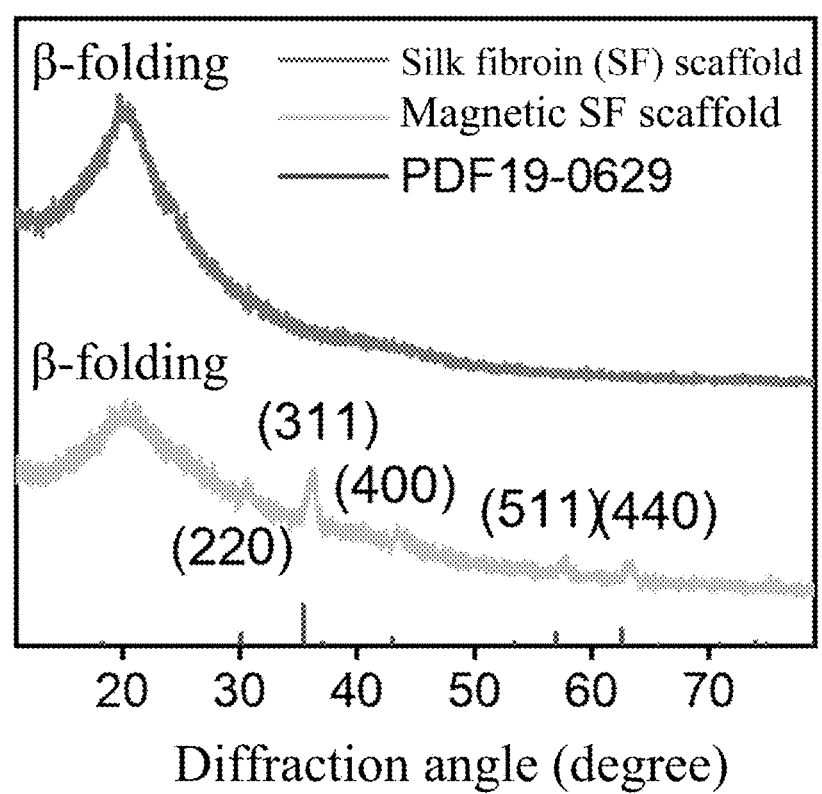
FIG. 6 shows an X-ray diffraction (XRD) pattern of a magnetic SF-based composite aerogel.

FIG. 6 shows an XRD pattern of a magnetic SF-based composite aerogel, and it can be seen from the XRD pattern that the magnetic SF-based composite aerogel includes SF and ferroferric oxide nanocubic particles.

Figure 7:
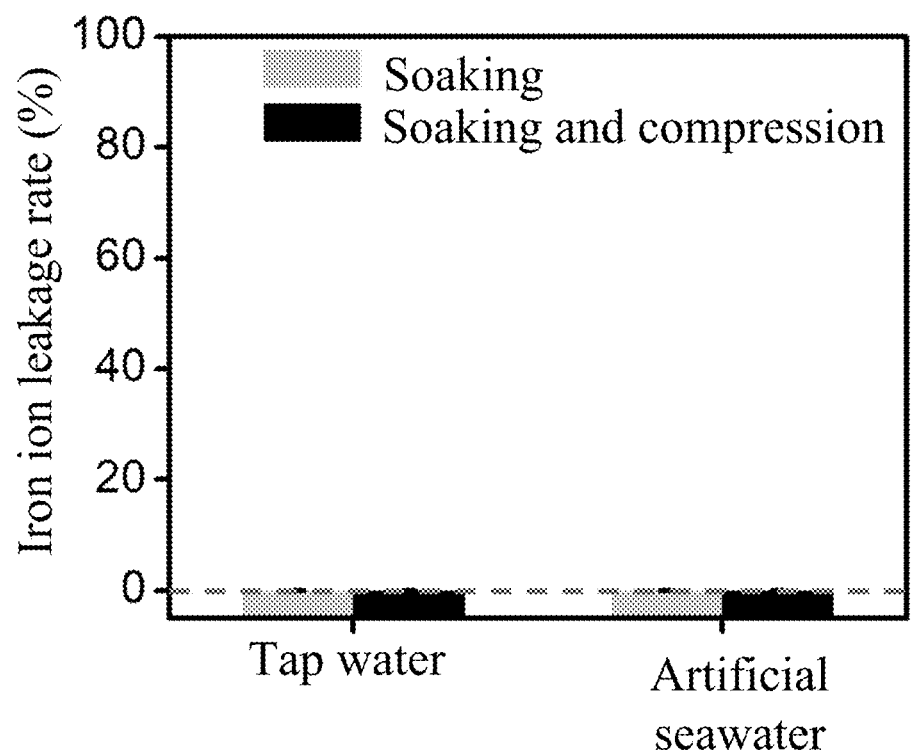
FIG. 7 shows the stability of a magnetic SF-based composite aerogel.

FIG. 7 shows the stability of a magnetic SF-based composite aerogel, where two experimental groups are set; in one experimental group, the magnetic SF-based composite aerogel was merely soaked for 7 d, and in the other experimental group, the magnetic SF-based composite aerogel was soaked and compressed for 7 d; and at the end of the experiment, a liquid was collected and tested for an iron ion concentration. It can be seen from the data in this figure that an iron ion concentration in a liquid is close to 0 in either of the above two experimental groups, indicating that the magnetic SF-based composite aerogel has excellent stability and does not release iron ions into a liquid environment when in use.

Example 4

The magnetic SF-based composite aerogels were subjected to photothermal temperature rise and water evaporation performance tests, and specific steps were as follows:

1) A xenon lamp was turned on, and when a light intensity of the xenon lamp was stabilized, the light intensity of the xenon lamp was adjusted to allow a light intensity of 1 kW/m$^2$ on an upper surface of an aerogel. The wet magnetic SF-based composite aerogels with different iron concentrations (0 mg/mL, 0.2 mg/mL, 0.5 mg/mL, 1.0 mg/mL, and 2.0 mg/mL) were placed in a center of a light spot, and a temperature change of an upper surface of each aerogel was recorded by a thermal infrared (TIR) camera for 1 h.
2) An electronic balance was placed below a xenon lamp (a light source) with a center of a light spot located in a center of a weigh pan of the electronic balance. A wet magnetic SF-based composite aerogel was placed in the center of the light spot. The xenon lamp was turned on, and when a light intensity of the xenon lamp was stabilized, the light intensity of the xenon lamp was adjusted to allow a light intensity of 1 kW/m$^2$ on an upper surface of the aerogel. After the aerogel was irradiated for 5 min, a reading on the electronic balance was recorded for 30 min, during which the reading was recorded every 30 s. The wet magnetic SF-based composite aerogels with different iron concentrations (0 mg/mL, 0.2 mg/mL, 0.5 mg/mL, 1.0 mg/mL, and 2.0 mg/mL) were tested, and three replicates were set for each sample.
3) Under irradiation by a xenon lamp, an ability of a magnetic SF-based composite aerogel to treat organic dye-containing wastewater simulated by an erythrosin-containing solution and an MB-containing solution was tested. The tested erythrosin-containing solution and MB-containing solution both had a concentration of 50 mg/L. A wastewater treatment ability of the magnetic SF-based composite aerogel was evaluated from two aspects.

Data Processing

Figure 8:
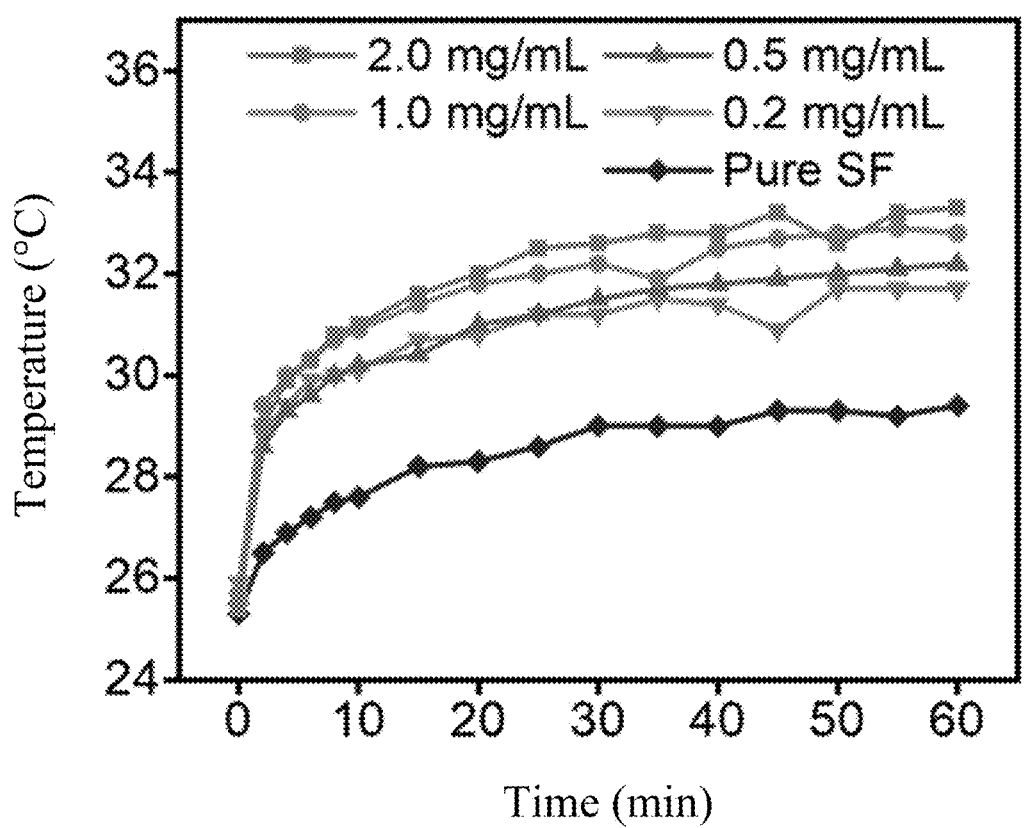
FIG. 8 shows photothermal temperature rise data of wet magnetic SF-based composite aerogels with different ferroferric oxide nanocubic particle concentrations.
Figure 9:
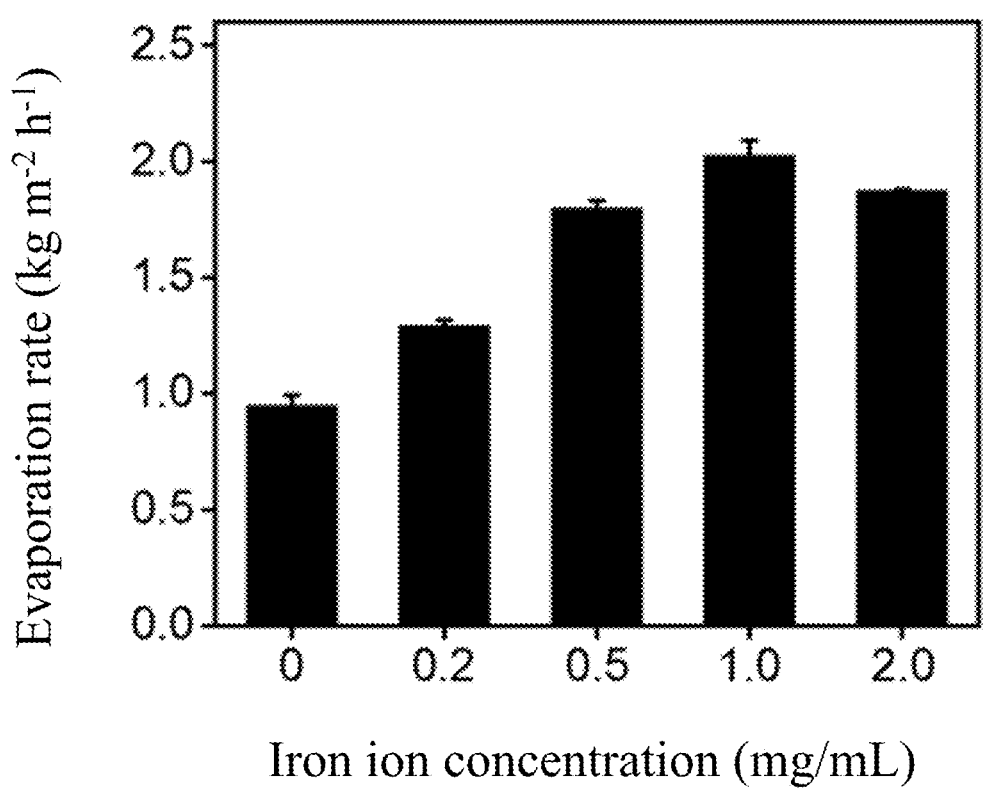
FIG. 9 shows water evaporation rates of wet magnetic SF-based composite aerogels with different ferroferric oxide nanocubic particle concentrations.

1) Results are shown in FIG. 8. It can be seen from FIG. 8 that a temperature of an upper surface of an aerogel first increases continuously over time and then is equilibrated, and an equilibrium temperature increases with the increase of an iron concentration in the aerogel.
2) Results are shown in FIG. 9. It can be seen from FIG. 9 that a water evaporation rate of an aerogel increases with the increase of an iron concentration in the aerogel, where a maximum water evaporation rate is allowed at an iron concentration of 1.0 mg/mL, and the water evaporation rate of the aerogel decreases slightly until the iron content raises to 2.0 mg/mL. Based on the above data, an optimal iron concentration in the aerogel of the present disclosure is 1.0 mg/mL.

Figure 10:
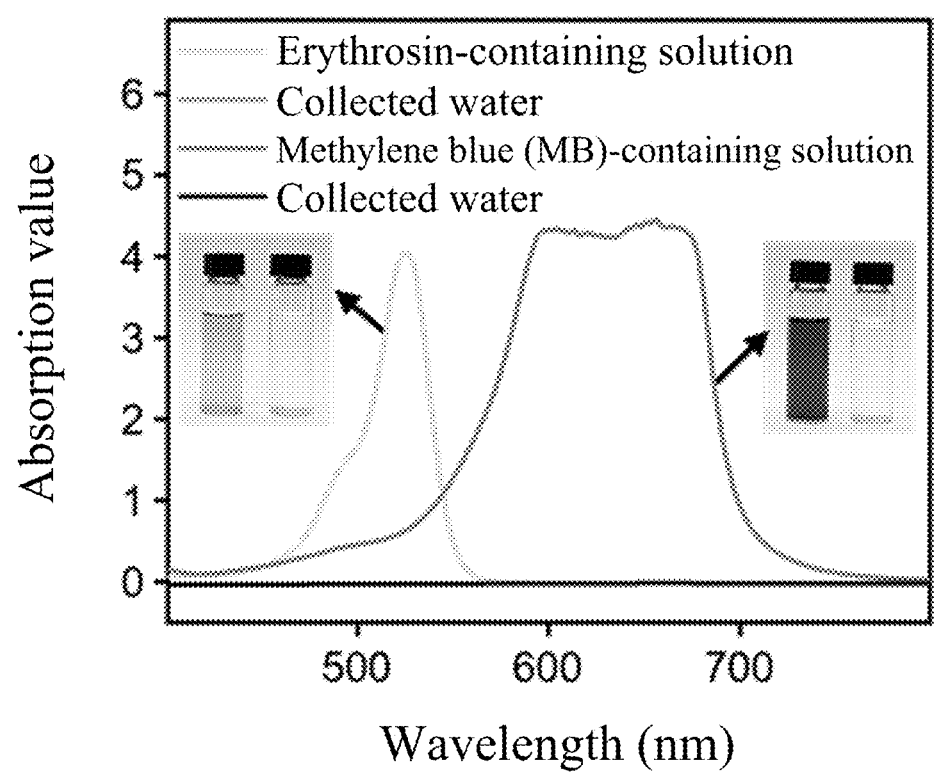
FIG. 10 shows ultraviolet-visible (UV-vis) spectra of a magnetic SF-based composite aerogel before and after treating an erythrosin-containing solution and an MB-containing solution.

3) Results are shown in FIG. 10.

It can be seen from the optical images of collected condensated water samples and original solutions that the original solutions are red and blue, respectively, and the collected condensated water samples all are clear, transparent, and colorless liquids. The dye-containing original solutions and the collected condensed water samples are subjected to UV-Vis absorption spectroscopy, and results show that UV-Vis absorption spectra of the collected condensed water samples have almost no characteristic absorption peaks of dyes, while the original solutions have obvious characteristic absorption peaks of dyes. It indicates that the aerogel still exhibits a specified purification effect for organic dye-containing wastewater.

Example 5

The magnetic SF-based composite aerogels were subjected to a magnetocaloric temperature rise performance test, and specific steps were as follows:

1) Under detection of an infrared (IR) thermal imager, an aerogel was exposed to a high-frequency magnetic field, and a magnetic field intensity was adjusted to 20 kA/m. The magnetic SF-based composite aerogels with different iron concentrations (0 mg/mL, 0.2 mg/mL, 0.5 mg/mL, 1.0 mg/mL, and 2.0 mg/mL) were wetted and then tested to determine magnetocaloric temperature rise performance for 30 min, during which a temperature was recorded every 1 min.

2) A magnetic SF-based composite aerogel with a ferroferric oxide nanocubic particle concentration of 1.0 mg/mL was adopted. The magnetocaloric temperature rise performance of the magnetic SF-based composite aerogel under different magnetic field intensities (10 kA/m, 15 kA/m, and 20 kA/m) was tested for 30 min, during which a temperature was recorded every 1 min.

Data Processing

Figure 11:
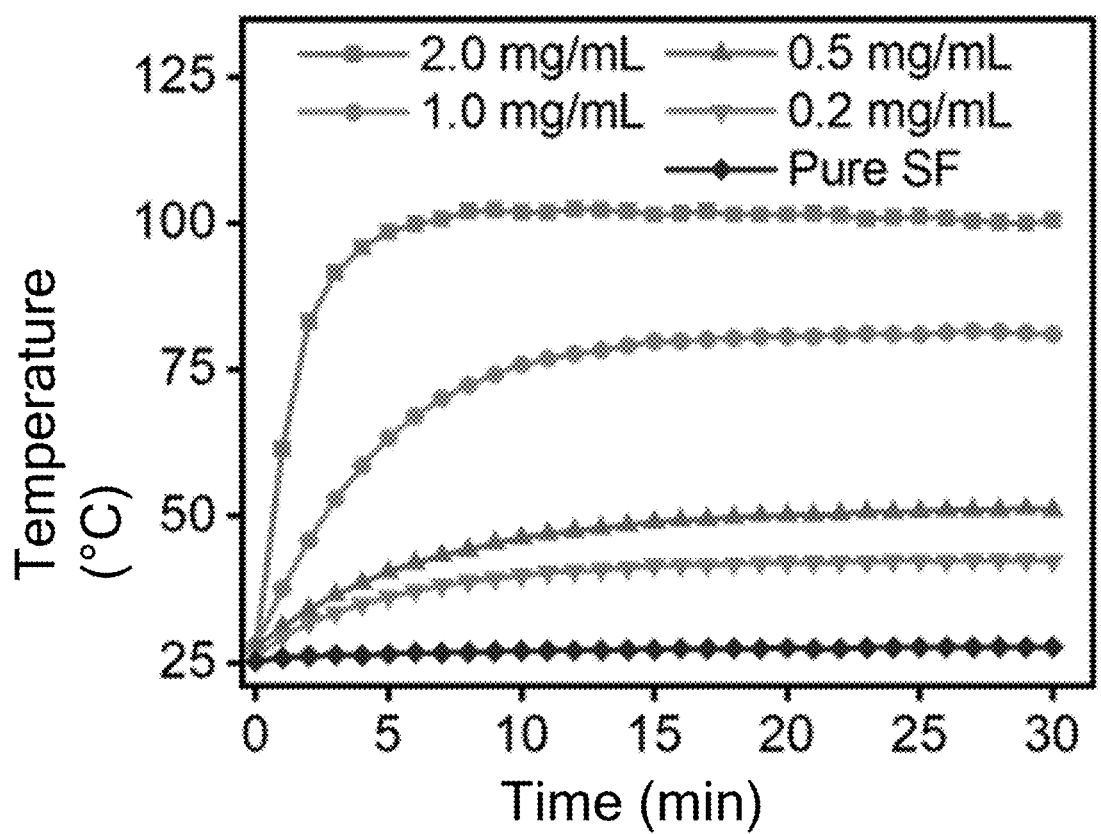
FIG. 11 shows magnetocaloric temperature rise curves of magnetic SF-based composite aerogels with different iron concentrations at a magnetic field intensity of 20 kA/m.

FIG. 11 shows magnetocaloric temperature rise data of the magnetic SF-based composite aerogels with different iron concentrations tested in the step 1) of Example 4, and it can be seen that a temperature rise of a sample increases with the increase of a ferroferric oxide nanocubic particle concentration in the sample.

Figure 12:
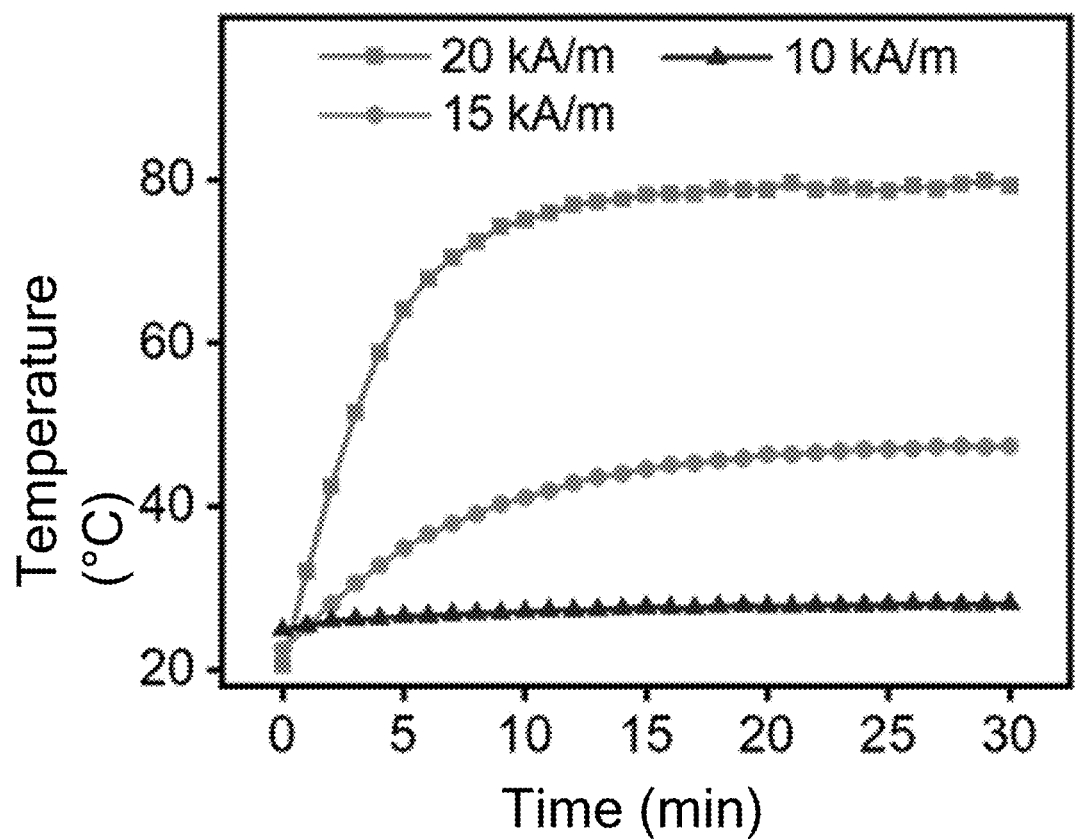
FIG. 12 shows magnetocaloric temperature rise curves of a magnetic SF-based composite aerogel with a ferroferric oxide nanocubic particle concentration of 1.0 mg/mL at different magnetic field intensities (10 kA/m, 15 kA/m, and 20 kA/m)

FIG. 12 shows magnetocaloric temperature rise data of the magnetic SF-based composite aerogel with a ferroferric oxide concentration of 1.0 mg/mL under different magnetic field intensities tested in the step 2) of Example 4, and it can be seen that a temperature rise of a sample increases with the increase of a magnetic field intensity.

Example 6

The magnetic SF-based composite aerogels were subjected to an antibacterial activity test under magnetocaloric assistance, and specific steps were as follows:

1) The magnetic SF-based composite aerogels with different iron concentrations (0 mg/mL, 0.2 mg/mL, 0.5 mg/mL, 1.0 mg/mL, and 2.0 mg/mL) were soaked in $10^5$ CFU/mL *E. coli* and *S. aureus* solutions for 1 h, then taken out and rinsed with sterilized water to remove bacteria on a surface of an aerogel, then placed in a 5 mL centrifuge tube, treated in an AC magnetic field for 30 min, cultivated in a clean liquid medium for 24 h, and coated on a plate, and then a bacterial concentration in a bacterial solution was deduced.

2) The magnetic SF-based composite aerogel with a magnetic ferroferric oxide nanocubic particle concentration of 1.0 mg/mL that was soaked in the bacterial solutions and rinsed in the step 1) was adopted. The magnetic SF-based composite aerogel was treated for 30 min in AC magnetic fields with different field intensities (10 kA/m, 15 kA/m, and 20 kA/m), then cultivated in a clean liquid medium for 24 h, and coated on a plate, and then a bacterial concentration in a bacterial solution was deduced.

3) Magnetic SF-based composite aerogels were soaked in $10^5$ CFU/mL *E. coli* and *S. aureus* solutions for 1 h, rinsed with sterilized water to remove bacteria on a surface of an aerogel, and then divided into two groups. Magnetic SF-based composite aerogels in one group were directly transferred to a fresh liquid medium. Magnetic SF-based composite aerogels in the other group were placed in a 5 mL sterilized centrifuge tube, then treated in an AC magnetic field for 30 min, and then transferred to a fresh liquid medium. Aerogels in the two groups were placed in a shaker at 37° ° C. for 72 h, then rinsed, immobilized, washed with gradient ethanol, and lyophilized. Resulting samples were observed by SEM.

Data Processing

Figure 13:
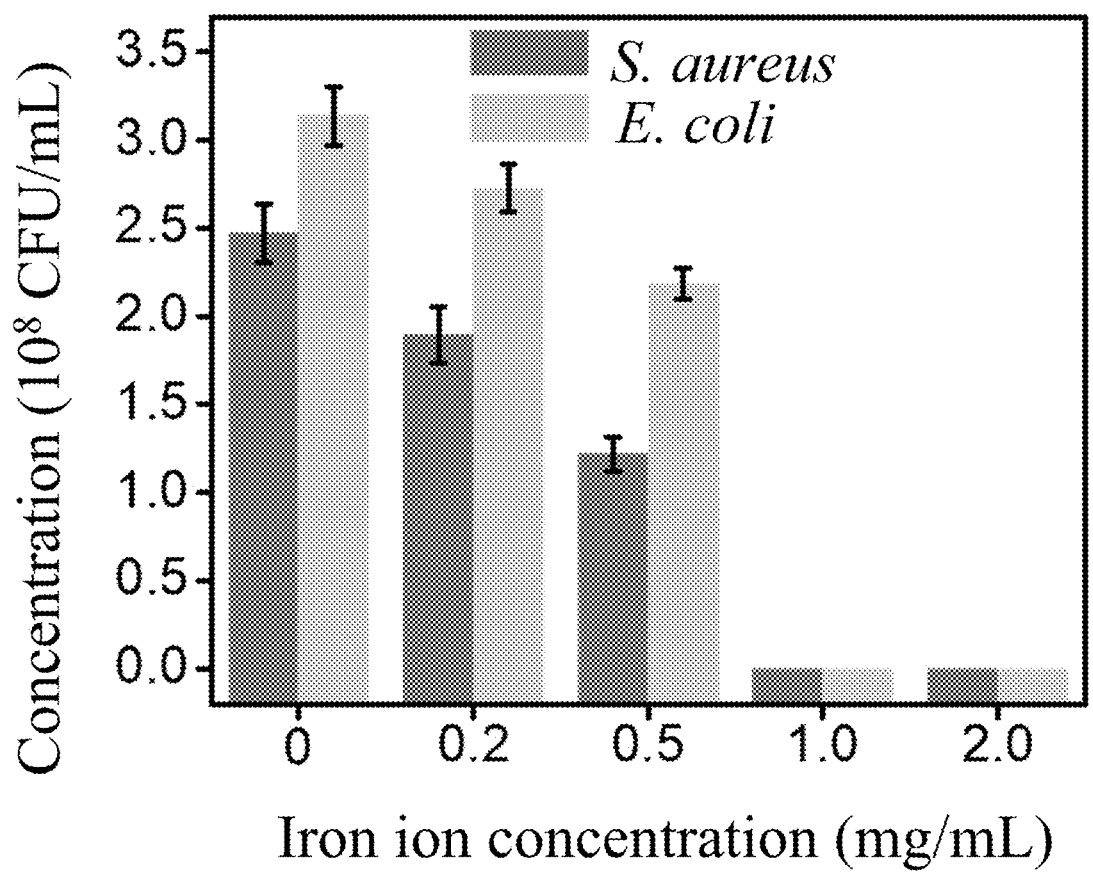
FIG. 13 shows bacterial concentration values in suspensions formed by cultivating the magnetic SF-based composite aerogels with different ferroferric oxide nanocubic particle concentrations that undergo a magnetocaloric treatment at a magnetic field intensity of 20 kA/m for 24 h.
Figure 14:
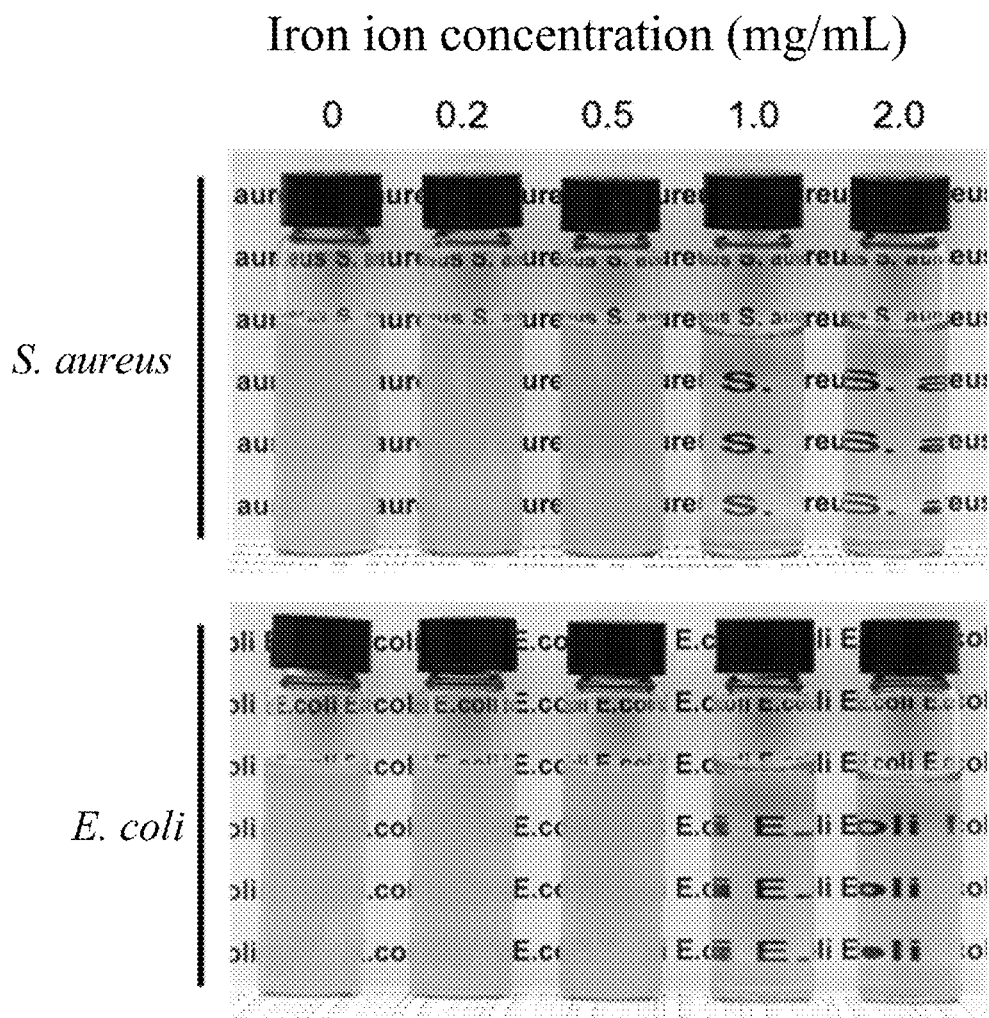
FIG. 14 shows optical images of suspensions formed by cultivating the magnetic SF-based composite aerogels with different ferroferric oxide nanocubic particle concentrations that undergo a magnetocaloric treatment at a magnetic field intensity of 20 kA/m for 24 h.

1) Results are shown in FIG. 13 and FIG. 14. It can be seen from FIG. 13 that bacterial concentrations in suspensions of aerogels with iron concentrations of 0 mg/mL, 0.2 mg/mL, and 0.5 mg/mL under a magnetic field intensity of 20 kA/m all are high, and bacterial concentrations in suspensions of aerogels with iron concentrations of 1.0 mg/mL and 2.0 mg/mL are basically 0. FIG. 14 shows optical images of suspensions of the aerogels corresponding to FIG. 13 after cultivation, and it can be seen that suspensions of aerogels with iron concentrations of 0 mg/mL, 0.2 mg/mL, and 0.5 mg/mL all are very turbid, while suspensions of aerogels with iron concentrations of 1.0 mg/mL and 2.0 mg/mL are very clear.

Figure 15:
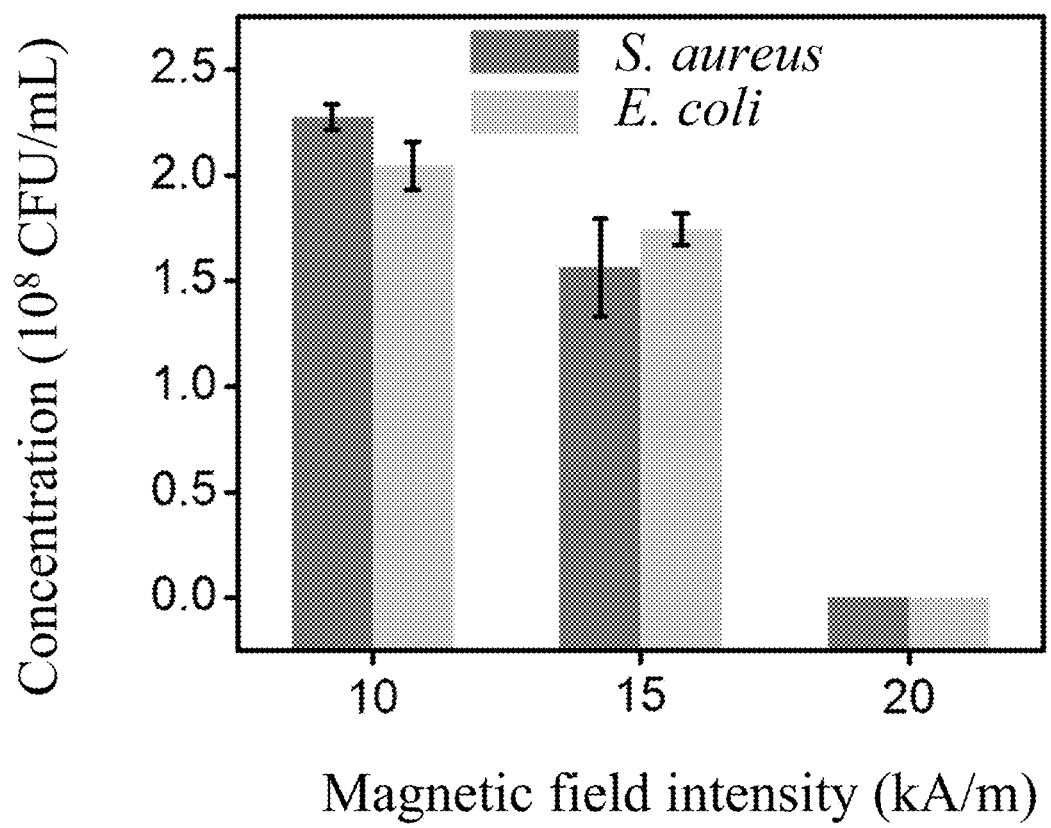
FIG. 15 shows bacterial concentration values in suspensions formed by cultivating the magnetic SF-based composite aerogel with a ferroferric oxide nanocubic particle concentration of 1.0 mg/mL that undergo a magnetocaloric treatment at different field intensities (10 kA/m, 15 kA/m, and 20 kA/m) for 24 h.
Figure 16:
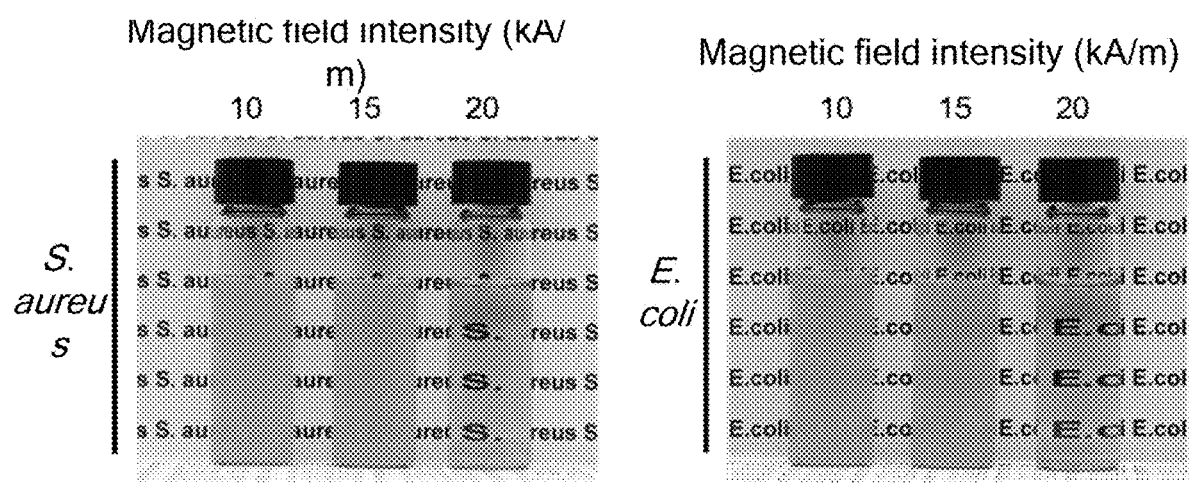
FIG. 16 shows optical images of suspensions formed by cultivating the magnetic SF-based composite aerogel with a ferroferric oxide nanocubic particle concentration of 1.0 mg/mL that undergo a magnetocaloric treatment at different field intensities for 24 h.

2) Results are shown in FIG. 15 and FIG. 16. It can be seen from FIG. 15 that bacterial concentrations in suspensions of the aerogel with a ferroferric oxide concentration of 1.0 mg/mL under magnetic field intensities of 10 kA/m and 15 kA/m all are very high, and a bacterial concentration in a suspension of the aerogel under a magnetic field intensity of 20 kA/m is basically 0. FIG. 16 shows optical images of suspensions of the aerogel corresponding to FIG. 15 after cultivation, and it can be seen that suspensions of the aerogel under magnetic field intensities of 10 kA/m and 15 kA/m all are very turbid, while a suspension of the aerogel under a magnetic field intensity of 20 kA/m is very clear.

Figure 17:
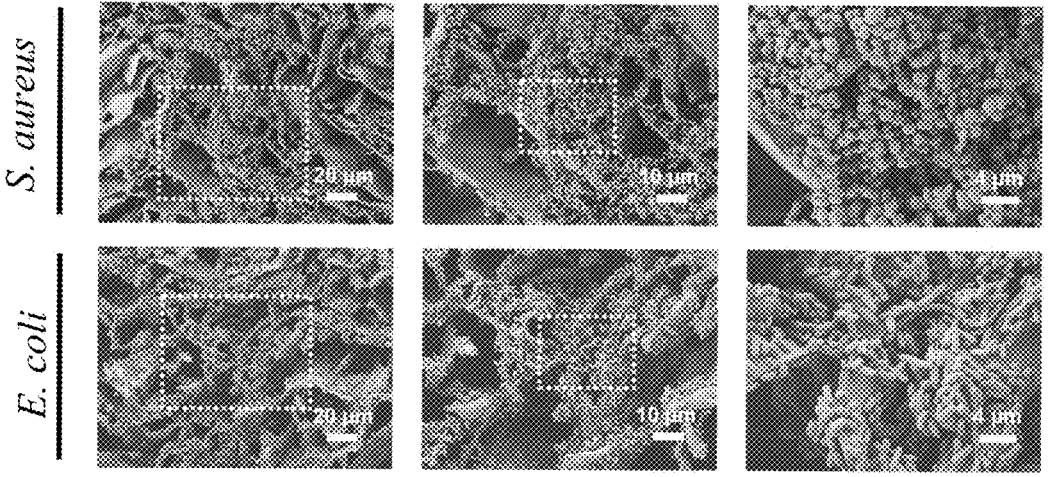
FIG. 17 shows scanning electron microscopy (SEM) images of bacteria-infected aerogels that undergo no magnetocaloric treatment and are incubated for 72 h.
Figure 18:
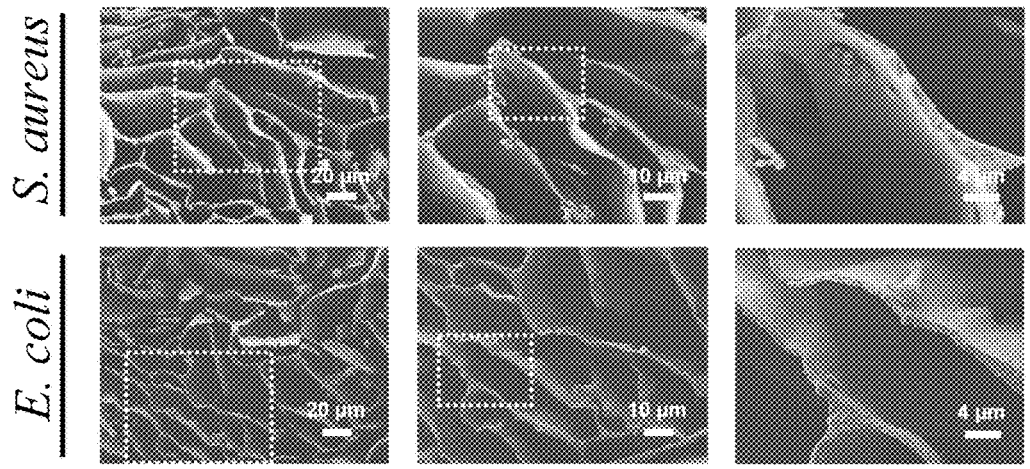
FIG. 18 shows SEM images of bacteria-infected aerogels that undergo a magnetocaloric treatment and are incubated for 72 h.

3) Results are shown in FIG. 17 and FIG. 18. It can be seen that there is basically no *E. coli* or *S. aureus* in pores of a magnetic SF-based composite aerogel undergoing a magnetocaloric treatment, and compared with a non-magnetocaloric treatment group, the magnetocaloric treatment can effectively kill *E. coli* and *S. aureus* to inhibit the formation of a biofilm.

Example 7

The magnetic SF-based composite aerogel was subjected to a magnetocaloric treatment and then a water evaporation performance test, and specific steps were as follows:

1) The magnetic SF-based composite aerogel with an iron concentration of 1.0 mg/mL was adopted in this test. Magnetic SF-based composite aerogels were soaked in $10^5$ CFU/mL *E. coli* and *S. aureus* solutions for 1 h, rinsed with sterilized water to remove bacteria on a surface of an aerogel, and then divided into two groups. A magnetic SF-based composite aerogel in one group was directly transferred to a fresh liquid medium. A magnetic SF-based composite aerogel in the other group was placed in a 5 mL sterilized centrifuge tube, then treated in an AC magnetic field for 30 min, and then transferred to a fresh liquid medium. Aerogels in the two groups were placed in a shaker at 37° C. for 72 h, and then taken out.

2) As described in Example 4, a xenon lamp was turned on, and when a light intensity of the xenon lamp was stabilized, the light intensity of the xenon lamp was adjusted to 1 kW/m². The magnetic aerogels in the step 1) were fixed in a water evaporation device and subjected to the water evaporation performance test.

Data Processing

Figure 19:
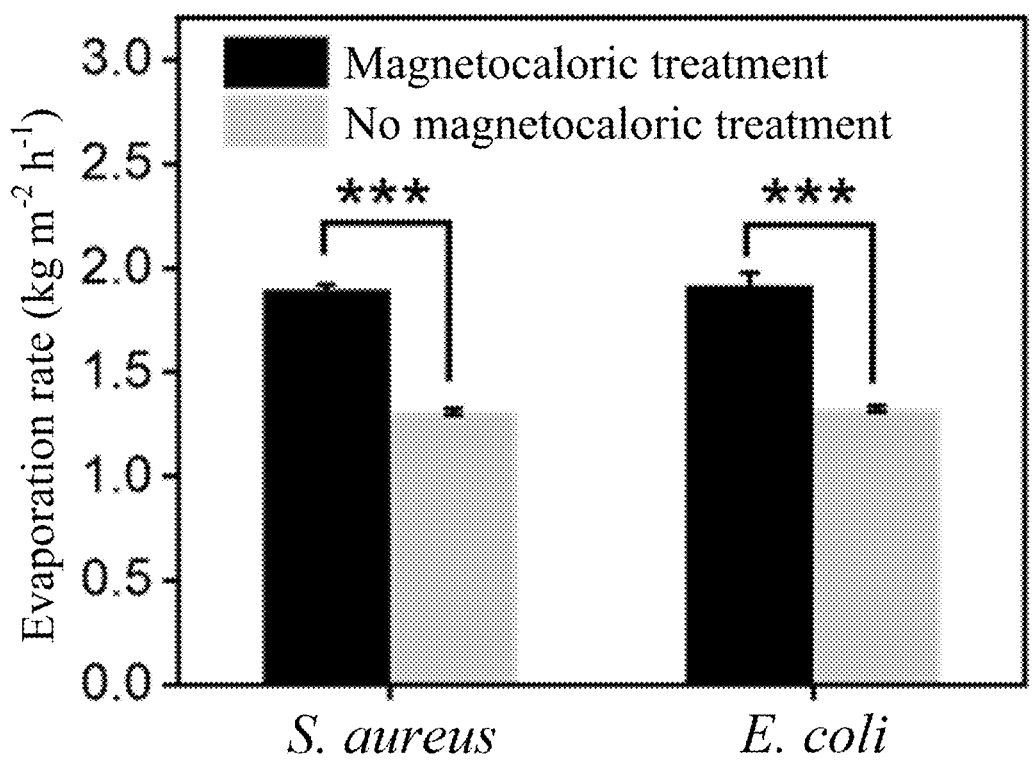
FIG. 19 shows the comparison of water evaporation performance between a magnetic SF-based composite aerogel undergoing a magnetocaloric treatment and a magnetic SF-based composite aerogel undergoing no magnetocaloric treatment that are incubated for 72 h.

Results are shown in FIG. 19. It can be seen from FIG. 19 that a water evaporation rate of the magnetic SF-based composite aerogel undergoing a magnetocaloric treatment is 93.6% to 94.6% of an initial water evaporation rate, and a water evaporation rate of the magnetic SF-based composite aerogel undergoing no magnetocaloric treatment is 64.5% to 65.0% of the initial water evaporation rate, indicating that the magnetocaloric treatment of the magnetic SF-based composite aerogel can effectively inhibit the production of biofouling inside the aerogel.

The above are merely preferred examples of the present disclosure, and are merely illustrative rather than restrictive. It should be understood by those skilled in the art that many alterations, modifications, or even equivalent replacements can be made within the spirit and scope defined by the claims of the present disclosure, but such alterations, modifications, or equivalent replacements fall within the protection scope of the present disclosure.

What is claimed is:

1. An anti-biofouling magnetic silk fibroin (SF)-based composite aerogel, consisting of an SF-aligned pore structure and magnetic nanoparticles (MNPs), wherein the MNPs are uniformly distributed in an inner pore of the SF-aligned pore structure;
   wherein the MNPs are ferroferric oxide nanocubic particles;
   a method for preparing the anti-biofouling magnetic SF-based composite aerogel comprises the following steps:
   S1: preparing hydrophobic magnetic ferroferric oxide nanocubic particles by a high-temperature oil-phase method, and encapsulating the hydrophobic magnetic ferroferric oxide nanocubic particles with a polymer to obtain hydrophilic magnetic ferroferric oxide nanocubic particles;
   S2: mixing the hydrophilic magnetic ferroferric oxide nanocubic particles obtained in the step S1 with an SF solution to obtain a mixed solution;
   S3: pouring the mixed solution obtained in the step S2 into a mold, conducting orientation freezing for 25 min to 35 min, and conducting lyophilization to obtain a first magnetic SF-based composite aerogel;
   S4: soaking the first magnetic SF-based composite aerogel obtained in the step S3 in a methanol solution to allow immobilization and washing to obtain a second magnetic SF-based composite aerogel; and
   S5: freezing the second magnetic SF-based composite aerogel obtained in the step S4, and conducting lyophilization to obtain the anti-biofouling magnetic SF-based composite aerogel for water treatment;
   the SF solution in the step S2 has a mass fraction of 6%;
   wherein a concentration of the ferroferric oxide nanocubic particles is 1.0 mg/mL, and a temperature rise of the anti-biofouling magnetic SF-based composite aerogel in a wet state under a magnetic field intensity of 20 kA/m is smaller than or equal to 81° C.

2. The anti-biofouling magnetic SF-based composite aerogel according to claim 1, wherein the anti-biofouling magnetic SF-based composite aerogel has a water evaporation rate of 2.03 kg·m⁻²·h⁻¹ under a light intensity of 1 kW/m².

* * * * *